United States Patent [19]

Renaud et al.

[11] 4,116,564
[45] Sep. 26, 1978

[54] APPARATUS FOR THE STUDY OF PLASMAS

[75] Inventors: Serge Renaud; Jean-Paul Rubel, both of Bron, France

[73] Assignee: Institut National de la Sante et de la Recherche Medicale Inserm, Paris, France

[21] Appl. No.: 655,394

[22] Filed: Feb. 5, 1976

[30] Foreign Application Priority Data

Feb. 12, 1975 [FR] France .................. 75 04904

[51] Int. Cl.$^2$ .................. G01N 21/00; G01J 3/48; G01N 21/24
[52] U.S. Cl. .................. 356/39; 356/73; 356/184; 356/197; 73/64.1
[58] Field of Search .................. G01N/5/02; 356/201, 356/39, 180, 208, 184, 197, 73; 259/DIG. 46; 73/64.1, 61.4

[56] References Cited

U.S. PATENT DOCUMENTS

| 3,635,678 | 1/1972 | Seitz | 356/39 |
| 3,972,614 | 8/1976 | Johanson | 356/73 |
| 3,997,272 | 12/1976 | George | 259/DIG. 46 |
| 4,037,972 | 7/1977 | Pross | 356/206 |

Primary Examiner—Vincent P. McGraw
Assistant Examiner—Rodney B. Bovernick
Attorney, Agent, or Firm—Fleit & Jacobson

[57] ABSTRACT

The apparatus comprises a massive body accurately maintained at 37° C and having a through horizontal bore in which are disposed in succession a bulb, a first concentrating lens, a test tube containing the sample, an interchangeable optical filter, a second concentrating lens and a photo-electric cell. The test tube is disposed in a blind vertical bore of the body and it contains a small stirrer bar resting on its bottom and made of a magnetic material. A permanent magnet, adapted to be operatively associated with the stirrer bar is rotated below the body, co-axially to the bar, by an electric motor at one of two accurately controlled speeds. The output of the cell is amplified and applied to one inlet of a differential amplifier the other inlet of which receives the output of a memory wherein the response of the cell has been registered at the beginning of a test. The outlet signal from the differential amplifier starts therefore from zero and may be applied to a usual graphically recording apparatus. For an aggregation test there is used a green filter and the motor is rotated at substantially 1100 rpm, while for a coagulation test the filter is violet and the motor rotates at 100 rpm.

5 Claims, 6 Drawing Figures

APPARATUS FOR THE STUDY OF PLASMAS

In the study of plasmas the susceptibility of blood plaquettes to aggregation and the coagulating time are to be determined for each sample. This has hitherto been effected successively by means of two separate apparatus, which is of course tedious and time consuming. Furthermore the known aggregometers and coagulometers are frequently inaccurate.

It is an object of the present invention to provide a method and an apparatus for the study of plasmas by means of which both aggregation and coagulation may be easily determined in an accurate manner.

Figure 1:
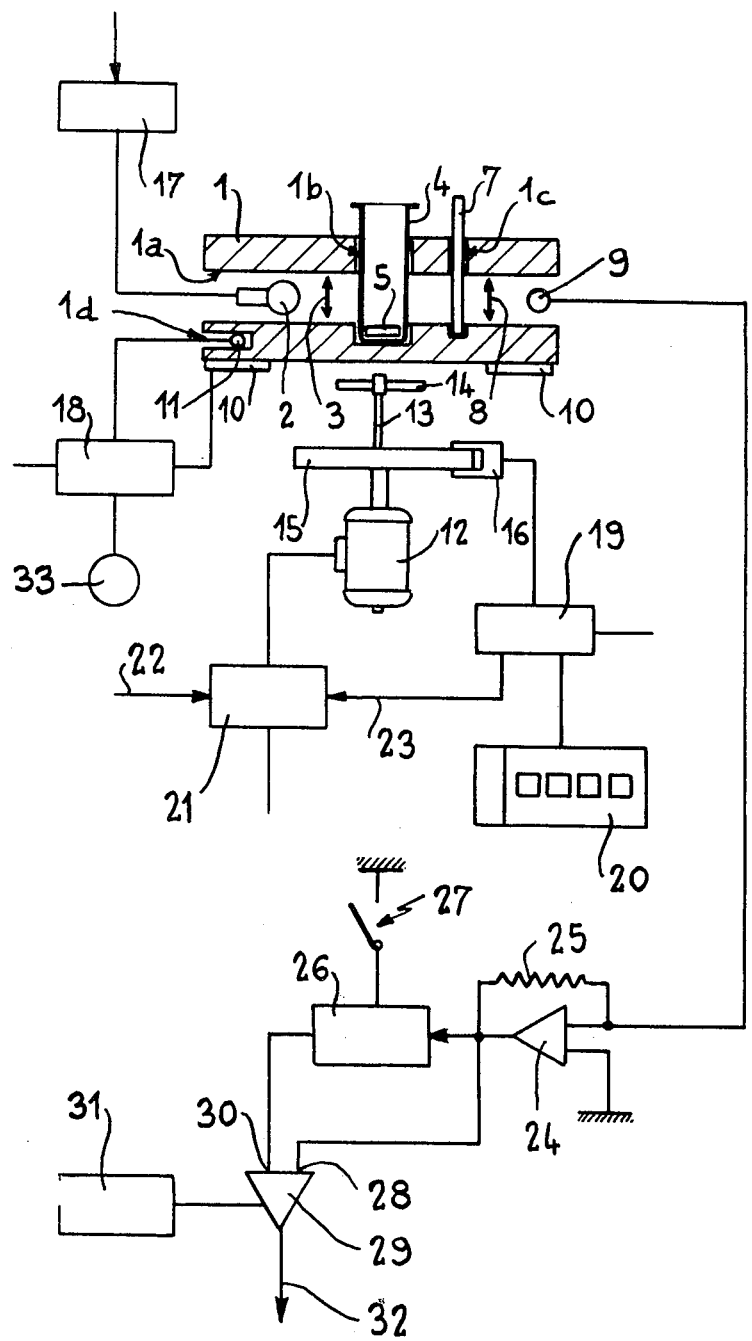
FIG. 1 is a general diagrammatical representation of an apparatus according to the present invention.

The apparatus illustrated in FIG. 1 comprises a massive body 1 made of a heat-conducting material. This body is formed with a horizontal through bore 1a and with a blind upwardly opening vertical bore 1b which intersects the former. There is further provided in body 1 an upwardly opening slit 1c which extends shortly below the horizontal bore 1a.

A light source in the form of a bulb 2 is disposed in the end of bore 1a opposed to slit 1c with respect to the vertical bore 1b. A lens 3 concentrates the light rays from bulb 2 in the form of a beam more or less parallel to the axis of bore 1a. The vertical bore 1b receives a transparent cylindrical test tube 4 which contains the sample to be tested. A small stirrer bar 5, made of iron or other magnetic metal is freely disposed horizontally on the flat bottom of tube 4. This bar may comprise a protective covering, if required. Its length is conveniently of substantially five millimeters with a transverse diameter of substantially one millimeter. An optical filter 7 is removably disposed in slit 1c. Beyond the latter bore 1a contains a concentrating lens 8 and a photo-electric cell 9 adapted to receive the light beam which has passed through the sample and through the optical filter 7.

Body 1 is further equipped with an electric heating device disposed on its lower side. It is further formed with a lateral blind bore 1d in which a thermometric detector 11 is mounted.

An electric motor 12 is disposed below body 1, coaxially with respect to the vertical bore 1b thereof. The upwardly extending shaft 13 of this motor carries a transverse permanent magnet 14 which thus rotates below the above-mentionned stirrer bar 5 on which it acts through the wall of body 1. The said bar 5 is thus caused to rotate together with shaft 13 when motor 12 is energized. Shaft 13 further carries a disc 15 which rotates between the branches of a speed detector 16 adapted to emit a series of signals the frequency of which corresponds to the angular speed of the shaft. This detector may be electromagnetic, disc 15 being formed with alternate zones of different permeability, or photo-electric, the successive zones of the disc being alternately transparent and opaque, black or white, etc.

Means are provided to avoid important eddy currents that may circulate in the portion of body 1 comprised between bar 5 and magnet 14, since such currents would form a magnetic screen between the said parts. For this purpose the said portion may be provided of quite reduced thickness, or it may be made of a metal of relatively high electric resistivity, or still further it may be laminated.

Turning now to the electric circuits associated with the apparatus described, bulb 2 receives its operating current from a source (not illustrated) through a regulating circuit 17 of high precision which maintains the intensity to a quite constant value during the test. Also the heating device 10 is energized through a regulator 18 which receives the information from the thermometric detector 11 and which maintains the temperature of body 1 to 37° C. ± 0.1° C. The signal issuing from the speed detector 16 is applied to the inlet of a chronometric counting circuit 19 which deduces therefrom the angular speed, for instance as the number of revolutions per minute.

The digital output of circuit 19 is applied at regular intervals of for instance one second, to a displaying circuit 20 comprising four luminescent digits. The speed of motor 12 is controlled by a speed regulating circuit 21 which is preferably in the form of a comparator with a first inlet 23 receiving the information from circuit 19, and a second inlet 22 to which a reference signal is applied.

The outlet signal from the photo-electric cell 9 is applied to the inlet of an amplifier 24 equipped with a linearizing feed-back circuit 25. The outlet of this amplifier is applied to a memory 26. The latter is actuated by a switch 27 and its output is permanently applied to the first inlet 30 of a differential amplifier 29 the second inlet 28 of which receives the output of the first amplifier 24. The gain of this differential amplifier 29 may be adjusted by a manually actuated circuit 31. Finally the output 32 of amplifier 29 is applied to any receiver desired, as for instance to a conventional graphically registering apparatus.

The general operation is as follows.

The test tube 4 containing a sample is positioned in bore 1b. Motor 12 is rotated at a constant speed accurately determined by the speed regulator 21. The permanent magnet 14 drives in synchronism the small bar 5 within the sample which is thus uniformly stirred during the whole test. The light beam concentrated by the lens 3 passes through the sample, then through the optical filter 7 and it reaches the photo-electric cell 9 which only receives the wave lengths corresponding to the filter. The signal emitted by cell 9 is amplified by amplifier 24 and it is simultaneously applied to the inlet of differential amplifier 24 and to the inlet of memory 26. The operator then actuates the switch 27 which causes the memory to register and to retain the amplified signal even after switch 27 is released. The first inlet 30 of differential amplifier 28 thus permanently receives a signal which corresponds to the signal of photo-electric cell 9 when switch 27 was actuated.

At the beginning of the operation the differential amplifier 29 therefore receives on its inlets two signals of equal value and its output is thus equal to zero. But as the transparency of the sample for the wave lengths corresponding to the optical filter 7 varies, the signal emitted by amplifier 24 also varies while the signal applied by memory 26 to the first inlet 30 of differential amplifier 29 remains constant. The signal which appears on the general outlet 32 of the apparatus therefore varies and its variations are representative of the variations in the transparency of the sample. The gain controlling circuit 31 permits of adapting this outlet signal to the receiving apparatus to which it is applied.

Experience demonstrates that it is thus possible to obtain curves corresponding to transparency variations with extremely well marked bends which accurately define the phenomena occuring during the test.

Figure 6:
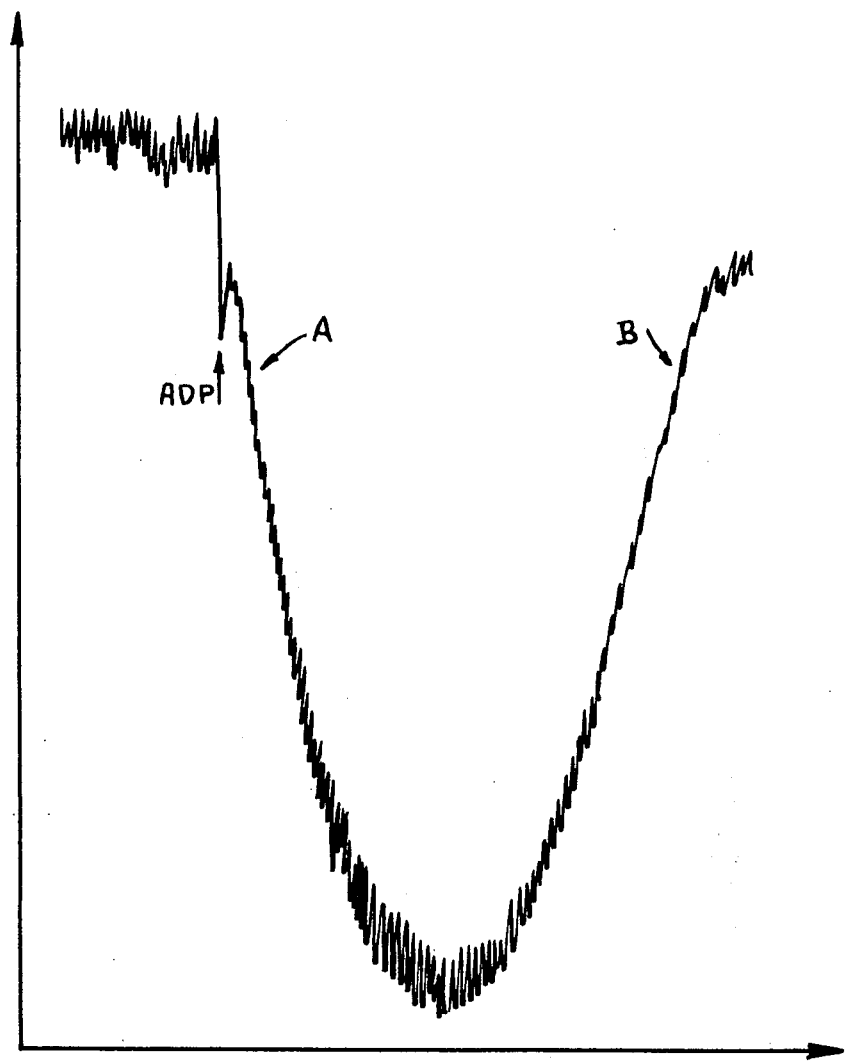
FIG. 6 illustrates a curve corresponding to an aggregation test.

More particularly, if the aggregation of a sample of plasma is to be studied, the apparatus is first started without the sample until body 1 has reached its normal operating temperature (37° C.). This may be indicated by a lamp 33 associated to the temperature regulating circuit 18. A green filter (band of about 530μ) is inserted into the slit 1c, and by means of inlet 22 a speed of 1100 rpm. is assigned to speed regulator 21. The plasma sample with blood plaquettes is poured into the test tube 4 and the small stirrer bar 5 is disposed in the sample. The test tube is then introduced into the vertical bore 1b where it is left for about 2 minutes in order that its temperature may become accurately stabilized at 37° C. Switch 27 is then actuated to bring to zero the output of differential amplifier 29. As a matter of safety the operator may verify that the successive actuations of the switch have no effect on the said output. The aggregating agent (ADP, thrombine, collagen) is added to the sample, motor 12 is started and the aggregation curve is registered. Such a curve has been illustrated in FIG. 6. The portion A of this curve corresponds to the aggregation step while the portion B corresponds to the disaggregation which does not always take place. The arrow ADP indicates the time at which this agent was added to the sample.

If it is desired to proceed to a coagulation step, there is used a violet filter (with a band of 360 to 400μ and quite opaque to infra-red). The speed of motor 12 is set to 100 rpm. The plasma sample is introduced into the test tube together with some NaCl (0.95%) and the tube is left in a heating block for about 10 minutes (incubation). It is thereafter transferred into bore 1b where it receives the stirrer bar 5. The apparatus is first set to zero by actuation of switch 27, as above explained. Motor 12 is then started and a M/25 solution of CaCl$_2$ is added to the sample. The arrow C in FIGS. 2 and 4 indicates the time of this addition which corresponds to the beginning of the coagulation step. The end of this step (i.e. the beginning of the formation of fibrine) is indicated by a sharp bend, as shown by arrow D. The coagulation time is of course represented by the horizontal distance between arrows C and D. It may be determined in a quite accurate manner.

Figure 2:
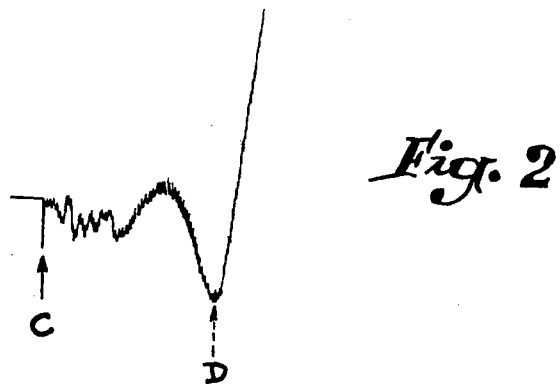
FIG. 2 shows a curve obtained in a coagulating test.
Figure 3:
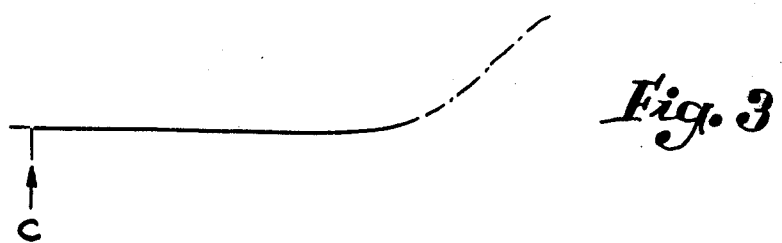
FIG. 3 shows comparatively the curve which is obtained for the same sample when the stirrer bar is stopped.
Figure 4:
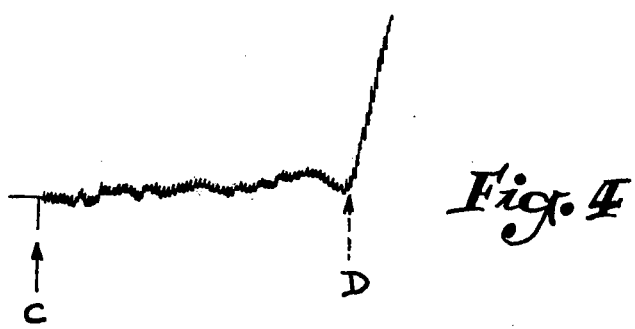
FIG. 4 illustrates another curve obtained in a second coagulating step.
Figure 5:
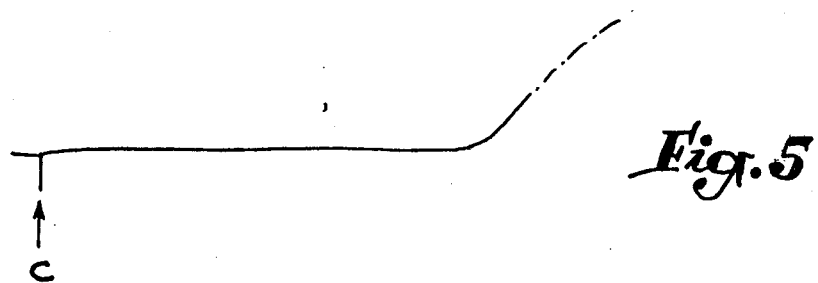
FIG. 5 shows the curve obtained with the sample of FIG. 4 when the stirrer bar is stopped.

For comparison purposes FIGS. 3 and 5 illustrate the curves obtained with the same samples as those corresponding respectively to FIGS. 2 and 4, but with motor 12 at standstill. The final bend is quite progressive and therefore the coagulation time cannot practically be measured. Moreover their comparison does not show that the coagulation time of the second sample is almost twice that of the first one.

We claim:
1. An apparatus for the study of the aggregation and coagulation of plasmas by conducting an aggregation test and conducting a coagulation test, said apparatus comprising:
   transparent container means for receiving a sample to be studied;
   means for maintaining said container means and said received sample at a predetermined constant temperature;
   light source means for generating a beam of light of constant intensity and for directing same towards said container means to cause same to pass through said received sample;
   rotatable stirrer means disposed within said container means for acting on said received sample;
   means for selectively rotating said stirrer means at two different constant speeds, namely a first speed of substantially 1100 rpm for an aggregation test and a second speed of substantially 100 rpm for a coagulation test;
   photo-electric means for receiving the light from said light source means which has passed through said container means and through said received sample and for delivering a signal in response thereto;
   means between said light source means and said photo-electric means for selectively receiving one of two different optical filters, namely a first one having a wave length of substantially 530μ (green) for an aggregation test and a second one having a wave length substantially from 360 to 400μ (violet) for a coagulation test;
   means for deriving an outlet signal from the signal of said photo-electric means;
   and means for zeroing the value of said outlet signal at the beginning of each test.
2. An apparatus as claimed in claim 1, wherein said rotatable stirrer means is a bar of substantially five millimeters in length with a diameter of substantially one millimeter.
3. An apparatus as claimed in claim 1, wherein said means for zeroing the value of said outlet signal at the beginning of each test comprises:
   a memory having an inlet and an outlet, the signal from said photo-electric means being applied to said inlet;
   a differential amplifier having first and second inlets and an amplifier outlet, with said first inlet being connected to the outlet of said memory, with said second inlet also receiving the signal from said photoelectric means and with said amplifier outlet generating said outlet signal;
   and means for causing said memory to register the signal applied to its inlet at the beginning of each test.
4. An apparatus as claimed in claim 3, wherein said differential amplifier has an adjustable gain.
5. An apparatus as claimed in claim 3, further comprising amplifier means interposed between said photoelectric means on the one hand, and the inlet of said memory and the second inlet of said differential amplifier on the other hand.

* * * * *